(12) United States Patent
Freeman

(10) Patent No.: US 6,694,187 B1
(45) Date of Patent: Feb. 17, 2004

(54) EXTERNAL DEFIBRILLATOR INSTRUCTION SYSTEM AND METHOD

(75) Inventor: Curtis W. Freeman, Windham, NH (US)

(73) Assignee: Koninklijke Philips Electronics N.V., Eindhoven (NL)

(*) Notice: Subject to any disclaimer, the term of this patent is extended or adjusted under 35 U.S.C. 154(b) by 217 days.

(21) Appl. No.: 09/603,270

(22) Filed: Jun. 23, 2000

(51) Int. Cl.$^7$ ............................................. A61N 1/39
(52) U.S. Cl. ............................................. 607/5
(58) Field of Search ........................... 607/7, 115, 145, 607/119, 2–5, 9, 14; 128/906, 920, 921–923; 600/508, 515–518

(56) References Cited

U.S. PATENT DOCUMENTS

| | | | |
|---|---|---|---|
| 5,163,429 A | * 11/1992 | Cohen | 607/4 |
| 5,381,803 A | 1/1995 | Herleikson et al. | 128/708 |
| 5,391,187 A | 2/1995 | Freeman | 607/5 |
| 5,735,879 A | 4/1998 | Gilner et al. | 607/7 |
| 5,836,993 A | 11/1998 | Cole | 607/59 |
| 6,304,773 B1 | * 10/2001 | Taylor et al. | 600/515 |
| 6,356,785 B1 | * 3/2002 | Snyder et al. | 607/5 |

* cited by examiner

*Primary Examiner*—George R. Evanisko

(57) ABSTRACT

The present disclosure relates to a system and method for instructing a user as to how to treat a patient with a defibrillator. In use, electrocardiogram data of the patient is analyzed to determine whether a shockable condition exists. Normal heart function and asystole are distinguished where no shock is advisable, and the user is advised that the patient is in asystole where an asystole condition is detected. Through this method, the attending technician is notified not only that a shock is not advised, but whether the shock is not advised due to an asystole condition.

18 Claims, 3 Drawing Sheets

EXTERNAL DEFIBRILLATOR INSTRUCTION SYSTEM AND METHOD

FIELD OF THE INVENTION

The present disclosure relates to an external defibrillator instruction system and method. More particularly, the disclosure relates to an external defibrillator system and method which provides details as to the patient's condition to the attending technician during no shock situations.

BACKGROUND OF THE INVENTION

Defibrillators supply pulses of electricity to a patient's heart to convert ventricular arrhythmias, such as ventricular fibrillation and ventricular tachycardia, to normal heart rhythms through the processes of defibrillations and cardioversion, respectively. There are two main classifications of defibrillators: external and implanted. Implanted defibrillators are surgically implanted into patients who have a high likelihood of needing electrotherapy in the future. Implanted defibrillators typically monitor the patient's heart activity and automatically supply electro-therapeutic pulses directly to the patient's heart when indicated. Thus, implanted defibrillators permit the patient to function in a somewhat normal fashion away from the watchful eye of medical personnel.

External defibrillators send electrical pulses to the patient's heart through electrodes which are applied to the patient's torso. External defibrillators are useful in the emergency room, emergency medical vehicles, and in other situations where there may be an unanticipated need to provide electrotherapy to a patient on short notice. The advantage of external defibrillators is that they may be used on a patient as needed, and then subsequently moved to be used with another patient.

External defibrillators can be broken down into two further categories: those for use by skilled medical personnel, and those for use by non-medical, yet properly trained, personnel. In the latter category, the defibrillators are often arranged as what is known as automatic external defibrillators (AEDs). With such "automatic" external defibrillators, the attending technician normally is provided with instructions produced by the defibrillator which advise the technician as to whether a shock should be delivered and when. Normally, such defibrillators primarily instruct the technician with a "no shock" message and a "shock" message. These messages typically are conveyed to the technician through a display on the device and/or with a voice prompt transmitted by the device.

Typically, automatic external defibrillators distinguish between ventricular fibrillation, ventricular tachycardia, asystole, and electromechanical dissociation/pulseless electrical activity to determine whether a shock should be administered. When ventricular fibrillation or ventricular tachycardia is detected, it is generally advisable to administer cardiopulmonary resuscitation (CPR) to the patient, secure the patient's airway, hyperventilate the patient with 100% oxygen, and defibrillate (i.e., shock) the patient up to several times (e.g., three times). When asystole or electromechanical dissociation is determined, CPR is generally advisable, although no shock should be delivered to the patient.

Although conventional automatic external defibrillators normally can determine which cardiac rhythms are appropriate for defibrillation and which rhythms are not and instruct the technician accordingly, the no shock messages provided by conventional automatic external defibrillators do not differentiate between asystole where there is no useful or detectable cardiac activity, and other non-shockable rhythms where the patient has an effective heart activity, such as normal sinus rhythm found in healthy individuals. As is known by those in the medical field, these rhythms indicate quite different patient conditions.

Because conventional automatic defibrillators do not communicate the distinct situations of asystole and normal sinus rhythm, their use is potentially hazardous in that it may cause an inappropriate response on the part of the technician. For instance, if the patient has effective heart activity, continued CPR on that patient is ill-advised. Such a situation could delay the transfer of the device to another patient in need of defibrillation. In addition, the technician may be tempted to deliver a further shock to the patient despite resumption of normal heart function, particularly where the technician is not highly trained. Where the patient has been in asystole for a prolonged period of time, it similarly is unnecessary for the technician to continue CPR in that the likelihood of the patient being revived is remote.

From the foregoing, it can be appreciated that it would be desirable to have an external defibrillator which not only distinguishes between asystole and normal sinus rhythm, but which also communicates which of these conditions is present to the technician when no shock is advised for the patient.

SUMMARY OF THE INVENTION

The present disclosure relates to a method for instructing a user as to how to treat a patient with a defibrillator. The method comprises analyzing electrocardiogram data of the patient to determine whether a shockable condition exists, distinguishing between normal heart function and asystole where no shock is advisable, and communicating to the user that the patient is in asystole where an asystole condition is detected. Through this method, the attending technician is notified not only that a shock is not advised, but whether the shock is not advised due to an asystole condition.

In view of the above method, the present disclosure also relates to an external defibrillator which comprises logic configured to analyze electrocardiogram data of the patient to determine whether a shockable condition exists, logic configured to distinguish between normal heart function and asystole where no shock is advisable, and logic configured to communicate to the user that the patient is in asystole where an asystole condition is detected.

The features and advantages of the invention will become apparent upon reading the following specification, when taken in conjunction with the accompanying drawings.

BRIEF DESCRIPTION OF THE DRAWINGS

The invention can be better understood with reference to the following drawings. The components in the drawings are not necessarily to scale, emphasis instead being placed upon clearly illustrating the principles of the present invention.

DETAILED DESCRIPTION

Figure 1:
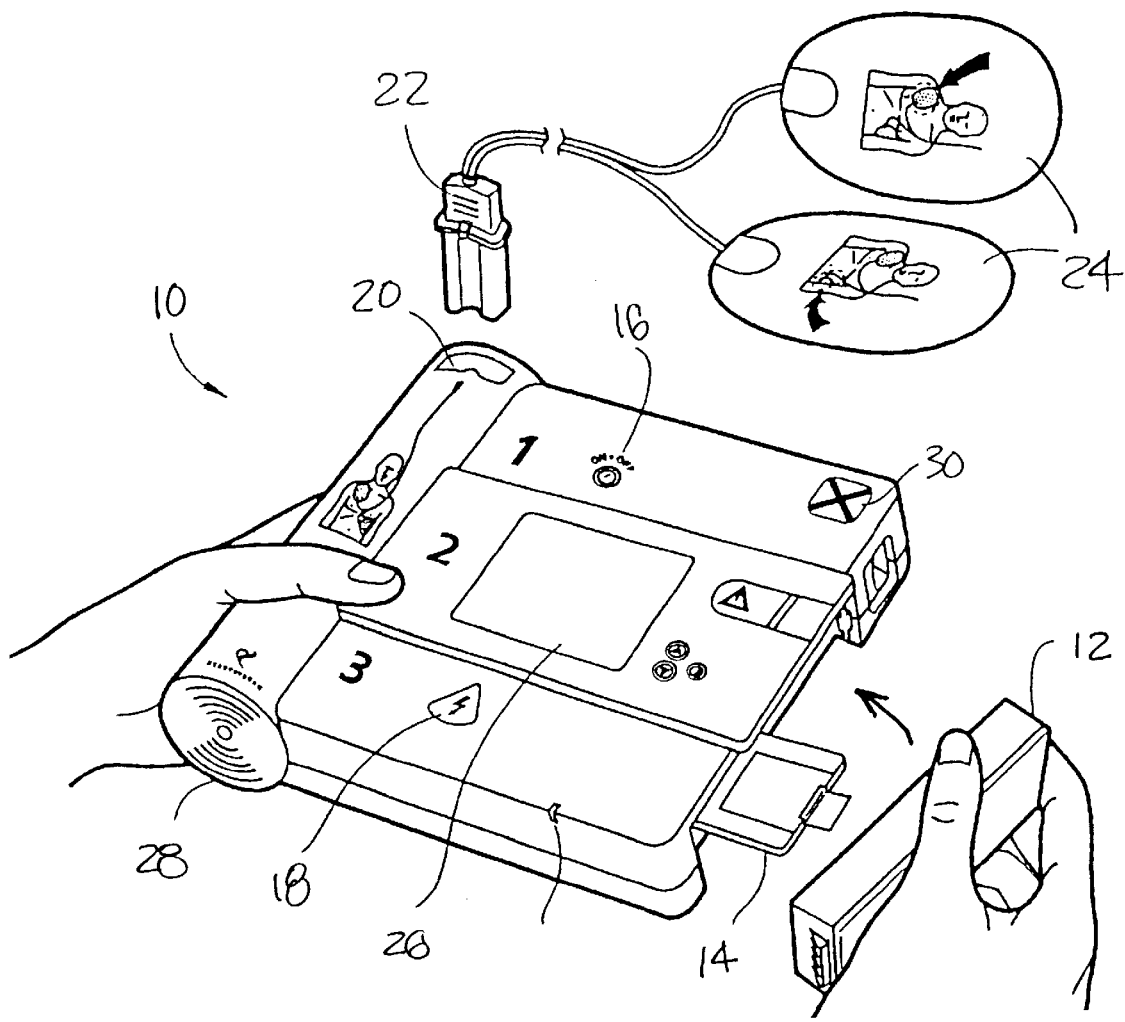
FIG. 1 is a perspective view of an external defibrillator constructed in accordance with the principles of the present invention.

Referring now in more detail to the drawings, in which like numerals indicate corresponding parts throughout the several views, FIG. 1 shows an external defibrillator 10 constructed in accordance with the principles of the present invention. Although the external defibrillator 10 shown in FIG. 1 is discussed in some detail herein, it is to be understood that this defibrillator 10 is illustrated and described for purposes of example only and that the principles and concepts discussed in the present disclosure apply equally to other defibrillators, as well as other emergency medical devices.

As indicated in FIG. 1, the external defibrillator 10 normally includes a detachable battery pack 12 which, when electrically connected to the defibrillator 10, initiates the defibrillator 10 and supplies power to it so that one or more shocks can be transmitted to a patient. The defibrillator 10 can also include a removable data card 14 which can be used to program the defibrillator 10 and/or provide for memory storage of monitored patient conditions. Located on the exterior of the defibrillator 10 is an on/off switch 16 which is used to turn the device on and off, and a shock button 18 which is used to initiate the transmission of a shock from the device to the patient. Normally formed in the device is a connector receptacle 20 which is adapted to receive a plug 22 of electrodes 24 which are placed on the patient prior to defibrillating the patient. Optionally, the defibrillator 10 can further include a display 26 and/or a speaker 28 which together or separately are used to communicate instructions to the attending technician. The display 26 can comprise a liquid crystal display (LCD) screen that displays text prompts, patient's information and event information, and electrocardiogram (ECG) data. Additionally, the defibrillator 10 can include a status display 30 which indicates the status of the defibrillator 10 to the technician. One example of a commercially available semi-automatic external defibrillator with the features and operation described above is a defibrillator sold under the brand name ForRunner which is currently commercially available from Agilent Technologies, Inc.

Figure 2:
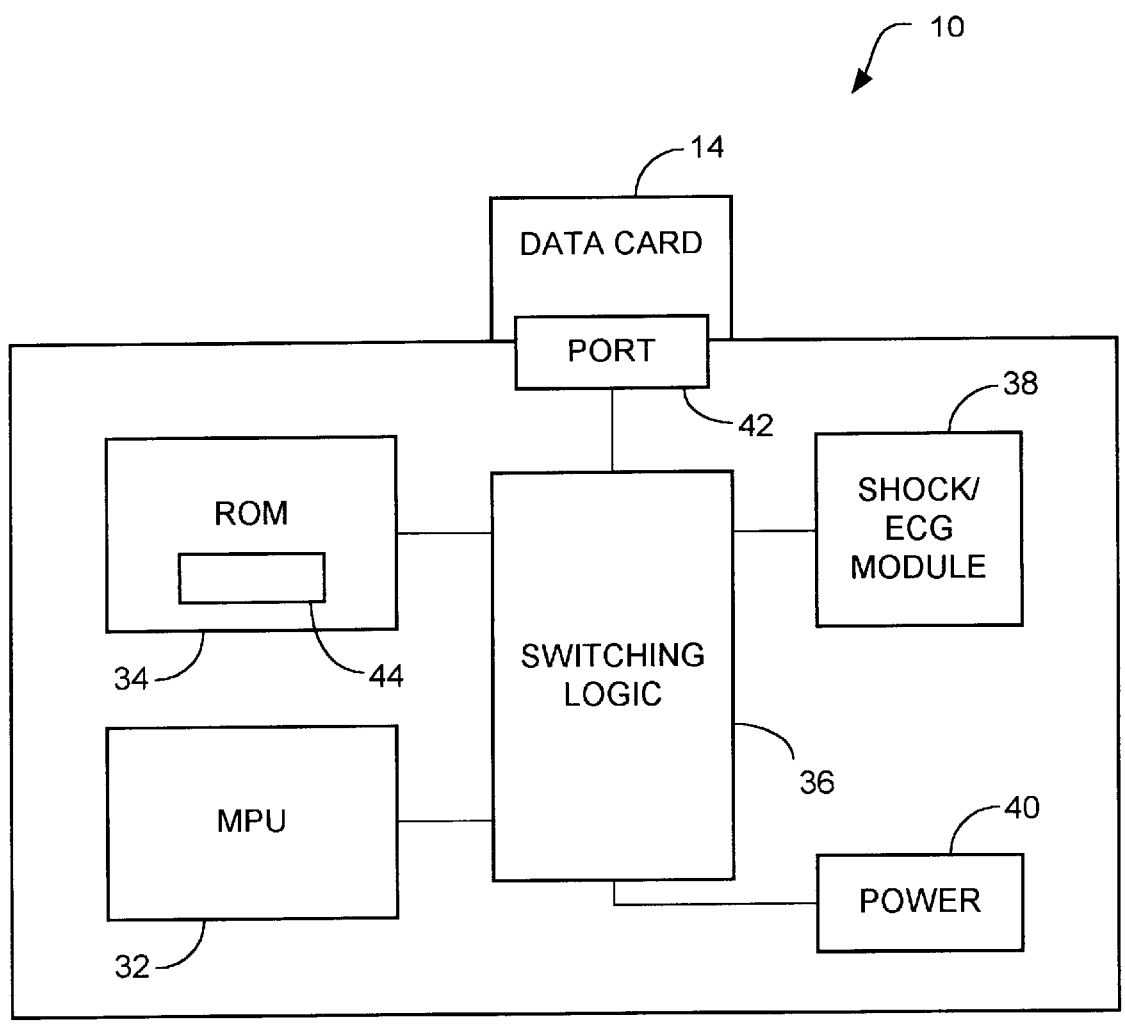
FIG. 2 is a block diagram of the external defibrillator shown in FIG. 1.

FIG. 2 illustrates the external defibrillator 10 of FIG. 1 in block diagram form. As shown in this figure, the external defibrillator 10 can include a microprocessor unit (MPU) 32 which is used to perform the program steps from software instructions contained, for example, in random access memory (ROM) 34. By way of example, these program steps can be performed by software 44 saved in the ROM. Switching logic 36 can provide an interface between the MPU 32 and a shock delivery/ECG module 38 to which defibrillation electrodes and/or monitoring electrodes (not shown) can be connected. The switching logic 36 further can control the delivery of energy from the power source 40 (e.g., battery 12) to the module 38. A memory port 42 can provide an interface between the removable data card 14 and the switching logic 36. As is discussed below, the defibrillator 10 typically can be operated in various modes. For instance, in a patient treatment mode, the MPU 32 and the switching logic 36 can interact to treat the patient and, optionally, record information such as patient ECG data and defibrillator operating parameters on the data card 14.

As will be appreciated by those having ordinary skill in the art, the defibrillator 10 typically is implemented in a combination of software and hardware. It is to be noted that the portions of the defibrillator implemented in software can be stored and transported on any computer-readable medium for use by or in connection with an instruction execution system, apparatus, or device, such as a computer-based system, processor-containing system, or other system that can fetch the instructions from the instruction execution system, apparatus, or device and execute the instructions. In the context of this disclosure, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CDROM) (optical).

When the defibrillator 10 is to be put to use, the battery 12 is first fitted into place within the defibrillator 10 in the manner indicated in FIG. 1. Once the battery 12 is inserted into place, the defibrillator 10 can automatically perform a comprehensive self test to ensure that proper operation of the defibrillator 10. By way of example, the self test can include two parts: an automatic self test followed by an interactive test. As will be appreciated by those having ordinary skill in the art, the automatic portion of the test can check for the presence of the data card 14 and its compatibility, as well as system functions such as available battery power. The interactive tests, on the other hand, can verify the correct operation of the display 26, buttons (such as the shock button 18), and light-emitting diodes (such as status display 30). Although such self tests are normally conducted, it will be understood by those having ordinary skill in the art that such tests could be bypassed by the attending technician in, for example, situations where immediate defibrillation is needed.

Figure 3:
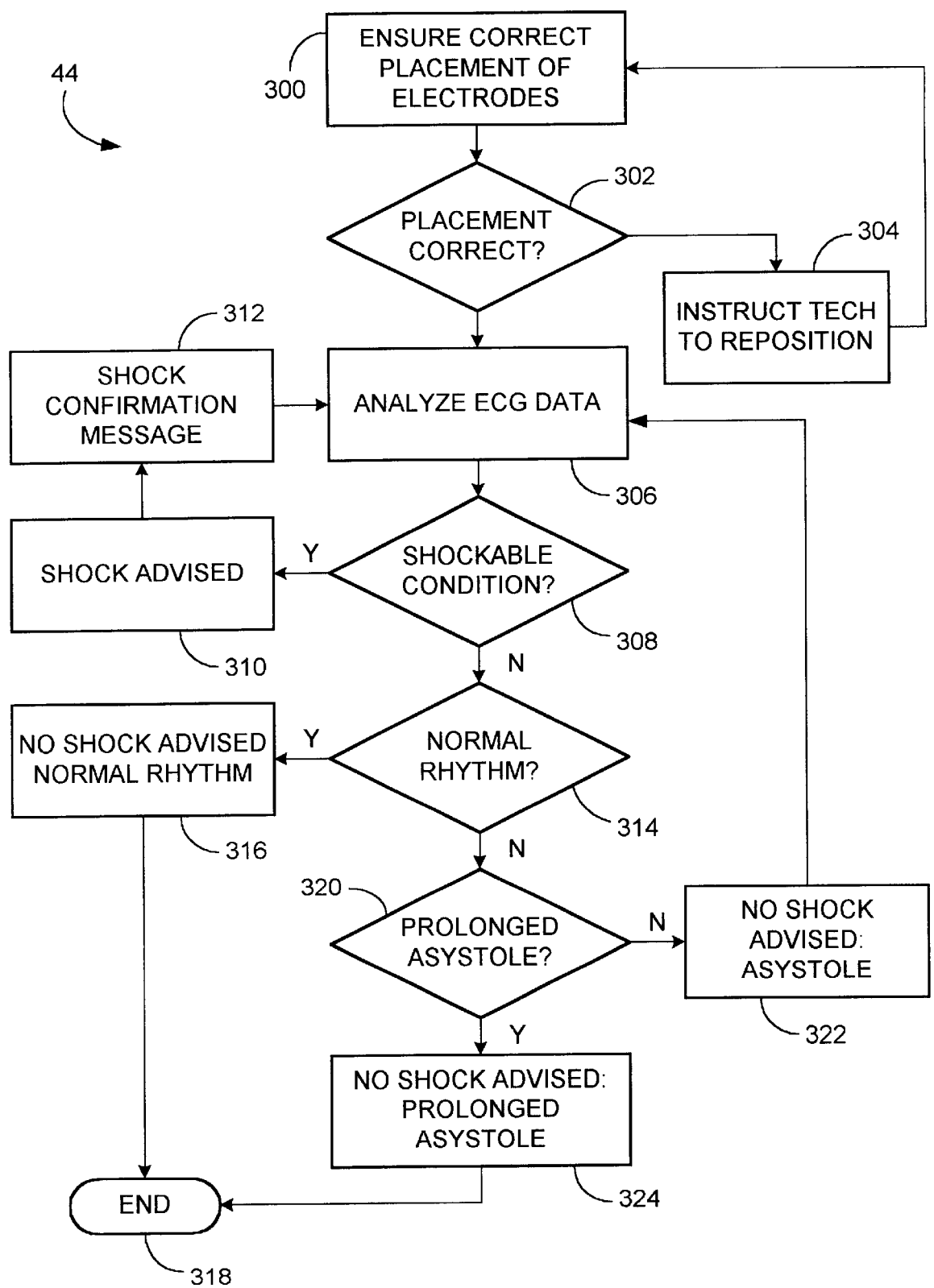
FIG. 3 is a flow diagram which illustrates an example embodiment of how the external defibrillator of the present invention is used.

When the defibrillator 10 is going to be used to defibrillate the patient, the technician inserts the electrode plug 22 into its receptacle 20 in the defibrillator 10, and places the electrodes 24 in place on the patient's torso. As is known by those having ordinary skill in the art, normally one electrode is placed just below the patient's right clavicle while the other is placed in line with the axilla and below the patient's left breast. Once the electrodes 24 are properly placed on the patient, with the external defibrillator 10 switched on, monitoring and treatment of the patient can begin. FIG. 3 provides a flow chart of an example embodiment of such monitoring and treatment of a patient. In particular, FIG. 3 shows the architecture, functionality, and operation of software 44 that can be saved in the memory 34 shown in FIG. 2. As indicated in block 300, the defibrillator 10 first determines whether the electrodes 24 are located in the right position on the patient's torso. By way of example, the defibrillator 10 can measure the impedance sensed by the electrodes 24 or auxiliary sensors (not shown) to ensure that the electrodes 24 are placed in the positions described in the foregoing. As indicated at 302, if the electrodes are not placed properly, the technician will be instructed to reposition them as indicated in block 304. After such repositioning has occurred, flow continues back to block 300 where the placement of the electrodes 24 is again checked. Once the electrodes 24 are placed in the correct positions, the defibrillator 10 then begins to analyze the electrocardiogram (ECG) data for the patient as indicated in block 306. This data can be obtained by the electrodes 24 or separate sensors (not shown) in a conventional manner.

As is known to those in the medical field, ECG data conveys a variety of information about the patient's cardia condition. For example, monitoring the ECG data for the patient can reveal normal sinus rhythm, ventricular fibrillation, ventricular tachycardia, and asystole. As is further known, the ventricular fibrillation and ventricular tachycardia conditions are treatable by delivering a shock, whereas the normal sinus rhythm and asystole conditions are not treatable by delivering shock. As indicated at 308, when a shock situation is encountered, the external defibrillator 10 instructs the attending technician to shock the patient by depressing the shock button 18 as indicated in block 310. As described above, these instructions can be visual instructions displayed on the display 26 and/or can be audible instructions transmitted over the speaker 28. After the shock button 18 has been depressed, a message can be provided to the technician to confirm that the shock was delivered as indicated in block 312. As this time, the defibrillator 10 continues to analyze the ECG data for the patient as indicated in block 306 to determine whether or not another shock should be delivered to the patient.

If, at 308, a shock situation is not advisable, flow continues to 314 where the device differentiates between normal sinus rhythm conditions and the asystole conditions. Where the no shock situation is created by normal sinus rhythm, i.e., normal healthy beating of the patient's heart, the system communicates a no shock message as identified in block 316. To avoid the ambiguity described in the background section of this disclosure, this no shock advised message typically includes an indication that normal sinus rhythm has resumed or equivalent message which indicates normal heart function of the patient. With such a message, the attending technician will not be tempted to shock the patient once more and will understand that the technician is now free to tend to other patients in need of medical attention, if any. At this point, the defibrillator 10 can be removed from the patient and the monitoring and treatment of the patient can cease as indicated at 318.

If the no shock condition does not result from normal sinus rhythm, i.e., the patient is in asystole, the attending technician is provided with a no shock message. Before providing such a message to the technician, a determination is made as to whether the asystole is persistent or prolonged, indicates that, in all likelihood, the patient has expired. To make this determination, the defibrillator 10 can be provided with appropriate hardware and/or software to record the duration of the asystole condition from its onset so that it can be determined how long the asystole has occurred. By way of example, if the asystole condition has continued for a predetermined duration of time, e.g. twenty minutes or more, continued medical attention to the patient can be determined to be futile. In a preferred embodiment, the defibrillator is configurable by the user so that this time period can be selected by the user. Alternatively, prolonged asystole can be diagnosed based upon the number of shocks that have been administered to the patient. As with the elapsed time embodiment, this number is preferably programmable by the user. During use, the elapsed time since the outset of asystole can be communicated to the technician via the display 26 and/or speaker 28. As indicated at 320, if the asystole condition is not persistent or prolonged, flow continues to block 322 and the attending technician is provided with a no shock message with a further indication that the patient is in asystole. This message can also recommend that resuscitation procedures, such as CPR, be instituted in an effort to revive the patient. Thereafter, the defibrillator 10 continues to analyze ECG data as indicated in block 306. If, however, the asystole condition is persistent or prolonged, the technician is provided with a no shock message which further identifies the persistent or prolonged asystole condition as indicated in block 324. In addition or in exception to this information, the message can identify to the technician that further attempts of resuscitation of the patient are ill-advised and that the technician should therefore cease such resuscitation attempts for this particular patient. At this point, therefore, the defibrillator 10 can be removed from the patient and the monitoring and treatment of the patient is terminated as indicated at 318.

While particular embodiments of the invention have been disclosed in detail in the foregoing description and drawings for purposes of example, it will be understood by those skilled in the art that variations and modifications thereof can be made without departing from the spirit and scope of the invention as set forth in the following claims.

What is claimed is:

1. A method for instructing a user as to bow to treat a patient with a defibrillator, comprising:

analyzing electrocardiogram data of the patient to determine whether a shockable condition exists;

based on the analyzing step, when a non-shockable condition exists, detecting whether the non-shockable condition is one of normal heart function and asystole;

communicating to the user that the patient is in asystole where an asystole condition is detected; and communicating to the user that normal heart function of the patient has resumed where normal heart function is detected, wherein when asystole is detected, determining whether the asystole qualifies as a prolonged asystole according to predetermined criteria, and communicating to the user that asystole endured by the patient comprises said prolonged asystole, and wherein the step of determining whether the asystole qualifies as a prolonged asystole comprises recording a duration of time from the onset of asystole.

2. The method of claim 1 wherein the predetermined time period for determining whether the asystole is a prolonged asystole is selected by the user.

3. The method of claim 1, further comprising instructing the user to administer cardio-pulmonary resuscitation (CPR) to the patient after it has been determined that asystole has been detected, and after a predetermined time period, communicating to the user that further administration of CPR is futile.

4. The method of claim 1, wherein the communicating to the user is visual via a display of the defibrillator.

5. The method of claim 4, wherein the communicating to the user via a display of the defibrillator comprises displaying the time elapsed since the onset of asystole.

6. The method of claim 1 wherein the communicating to the user is audible via a speaker of the defibrillator.

7. The method of claim 6, wherein the communicating to the user via a speaker of the defibrillator comprises audibly announcing the time elapsed since the onset of asystole.

8. An external defibrillator comprising:

electrocardiogram means for performing an electrocardiogram on a patient;

a first logic configured to analyze electrocardiogram data of the patient from said electrocardiogram means to determine whether a shockable condition exists;

a second logic configured to detect either of a normal heart function and an asystole and distinguish between the normal heart function and the asystole when the first logic has determined that no shockable condition exists;

a third logic configured to communicate to the user that
the patient is in asystole when an asystole condition is
detected by the second logic;

a fourth logic configured to communicate to the user that
normal heart function of the patient has resumed where
normal heart function is detected by the third logic; and logic configured to determine, according to a predetermined criteria, and to communicate, to the user, that the
patient has endured a prolonged asystole,
wherein the predetermined criteria for determining that
the prolonged asystole has occurred includes a measurement of a duration of time from the onset of
asystole by the second logic.

9. The defibrillator of claim 8, further comprising a
display that is connected electrically to the fourth logic to
display an indication to the user whether the patient has
either an asystole condition or normal heart function.

10. The defibrillator of claim 8, further comprising a
speaker that is connected electrically to the fourth logic to
audibly alert the user whether the patient has either an
asystole condition or normal heart function.

11. The defibrillator of claim 8, wherein the defibrillator
comprises an automatic external defibrillator.

12. An external defibrillator comprising:

electrocardiogram means for performing an electrocardiogram on a patient;

means for analyzing electrocardiogram data of the patient
from said electrocardiogram means to determine
whether a shockable condition exists;

means for detecting a normal heart function and an
asystole when no shock is advisable based on the
determination of the means for analyzing;

means for communicating to the user that the means for
detecting has detected that:
(a) the patient is in asystole when an asystole condition
is detected; and
(b) the patient has resumed where normal heart function where normal heart function is detected; and means for communicating to the user that the patient has
endured a prolonged asystole according to a predetermined criteria,
wherein the prolonged asystole is determined from a
duration of time from the onset of asystole detected
by the means for detecting.

13. The defibrillator of claim 12, wherein the means for
communicating comprises a display for displaying to the
user whether the patient has one of an asystole condition and
normal heart function.

14. The defibrillator of claim 12, wherein the communicating means further comprises means for audibly communicating to the user whether the patient has one of an
asystole condition mid normal heart function.

15. The defibrillator of claim 12, wherein the defibrillator
comprises an automatic external defibrillator.

16. A computer readable medium comprising:

a program for performing an electrocardiogram on a
patient;

logic configured to analyze electrocardiogram data of the
patient after the electrocardiogram program has begun
to determine whether a shockable condition exists;

logic configured to detect a normal heart function and an
asystole where no shock is advisable;

communication logic configured to communicate to the
user that the patient:
(a) is in asystole when an asystole condition is detected;
and
(b) normal heart function has resumed when such a
condition is detected, logic configured to communicate to the user that the
asystole endured by the patient is identified as an
prolonged asystole according to predetermined criteria,
wherein the predetermined criteria fir determining that
the prolonged asystole has occurred is determined by
a duration of time from the onset of the asystole.

17. The computer readable medium of claim 16, wherein
the communication logic is configured to request a display
to the user as to whether a shockable or nonshockable
condition exists, and if the request is to display a nonshockable condition, said communication logic further
includes an indication whether the non-shockable condition
comprises one of a normal heart function and an asystole.

18. The computer readable medium of claim 16, wherein
the communication logic is configured to request an audible
communication to the user as to whether a shockable or
nonshockable condition exists, and if the request is to
communicate a non-shockable condition, said communication logic further includes an indication whether the non-shockable condition comprises one of a normal heart function and an asystole.

* * * * *